(12) United States Patent
Anker

(10) Patent No.: US 11,377,300 B2
(45) Date of Patent: Jul. 5, 2022

(54) TRANSPORT SYSTEM FOR STERILE PROCESSING DEPARTMENT

(71) Applicant: Gibotech A/S, Odense SØ (DK)

(72) Inventor: Henrik Anker, Odense SØ (DK)

(73) Assignee: Gibotech A/S, Odense SØ (DK)

( * ) Notice: Subject to any disclaimer, the term of this patent is extended or adjusted under 35 U.S.C. 154(b) by 0 days.

(21) Appl. No.: 17/220,555

(22) Filed: Apr. 1, 2021

(65) Prior Publication Data

US 2021/0309461 A1 Oct. 7, 2021

(30) Foreign Application Priority Data

Apr. 3, 2020 (EP) .................................. 20167998.2

(51) Int. Cl.
| | |
|---|---|
| *B65G 17/12* | (2006.01) |
| *A61B 50/30* | (2016.01) |
| *A61L 2/26* | (2006.01) |
| *G05D 1/02* | (2020.01) |
| *B08B 13/00* | (2006.01) |
| *G06Q 10/08* | (2012.01) |

(52) U.S. Cl.
CPC .............. *B65G 17/12* (2013.01); *A61B 50/30* (2016.02); *A61L 2/26* (2013.01); *G05D 1/02* (2013.01); *B08B 13/00* (2013.01); *B65G 2201/0235* (2013.01); *G06Q 10/08* (2013.01)

(58) Field of Classification Search
CPC ............ B65G 17/12; B65G 2201/0235; A61B 34/00; A61B 50/30; A61B 90/70; A61B 90/92; A61L 2/26; G06Q 10/08; G06Q 50/28; B08B 13/00; G05D 1/02
See application file for complete search history.

(56) References Cited

U.S. PATENT DOCUMENTS

| | | | | |
|---|---|---|---|---|
| 3,453,659 A | * | 7/1969 | Otte | .......................... E04H 3/08 |
| | | | | 104/307 |
| 4,643,303 A | * | 2/1987 | Arp | .......................... A61L 2/26 |
| | | | | 206/370 |

(Continued)

FOREIGN PATENT DOCUMENTS

| | | |
|---|---|---|
| DE | 102017209966 A1 | 12/2018 |
| EP | 3550486 A1 | 10/2019 |
| WO | 2017077073 A1 | 5/2017 |

*Primary Examiner* — James R Bidwell
(74) *Attorney, Agent, or Firm* — Fox Rothschild LLP; Carol E. Thorstad-Forsyth

(57) ABSTRACT

Disclosed is a transport system for handling a plurality of different types of containers for medical equipment in a sterile processing department, the system comprises: a plurality of containers of a first type and a plurality of containers of a second type; conveyor stations for the plurality of containers, the conveyor stations being configured to transport the first type of containers and/or the second type of containers relative to the conveyor station; and a transport tray for supporting the first type of containers and the second type of containers, the transport tray having a set of securing elements configured to releasably secure the first type of containers to the transport tray and the second type of containers to the transport tray. The conveyor station is configured to transport the first type of containers and/or the second type of containers secured to the transport tray.

12 Claims, 4 Drawing Sheets

(56) References Cited

U.S. PATENT DOCUMENTS

| | | | | |
|---|---|---|---|---|
| 5,511,594 | A | * | 4/1996 | Brennan .................. A61J 3/00 141/100 |
| 5,896,297 | A | * | 4/1999 | Valerino, Sr. .... G05B 19/41895 700/213 |
| RE42,730 | E | * | 9/2011 | Lasher ................... B65B 61/20 53/474 |
| 8,261,515 | B2 | * | 9/2012 | Stemmle ............... B65H 31/34 53/473 |
| 10,053,248 | B2 | * | 8/2018 | Joplin ..................... G07F 11/52 |
| 10,086,974 | B2 | * | 10/2018 | Joplin .................... B65D 19/44 |
| 10,575,933 | B2 | * | 3/2020 | Berg ...................... A61B 50/34 |
| 10,842,894 | B1 | * | 11/2020 | Provost ................... A61L 2/10 |
| 2008/0271971 | A1 | | 11/2008 | Schuck et al. |
| 2020/0399010 | A1 | * | 12/2020 | Velagapudi ............ B65D 25/10 |
| 2021/0236236 | A1 | * | 8/2021 | Van Den Houdt ..... A61L 2/202 |

* cited by examiner

TRANSPORT SYSTEM FOR STERILE PROCESSING DEPARTMENT

CROSS-REFERENCE TO RELATED APPLICATIONS

The present application claims priority to European Patent Application No. 20167998.2, filed on Apr. 3, 2020. The content of this application is incorporated herein by reference in its entirety.

FIELD

The present invention relates to a transport system for handling a plurality of different types of containers for medical equipment in a sterile processing department for sterilizing medical equipment, and to a transport tray for use in such a system.

BACKGROUND

Increasing healthcare cost is global problem which every country face. Automation of manual process in hospitals can be part of the solution. However, due to the high complexity of hospitals the degree of atomization until now has been low.

Processes in hospitals often requires handling of equipment made from a significant number of different suppliers making automation difficult. Furthermore, having automated systems that are locked to a specific supplier of equipment is typically not acceptable from an economical viewpoint.

Cleaning and sterilizing of medical equipment such as endoscopes and surgical instruments in a sterile processing department is an example of a work intensive process. Today used medical equipment is typically provided to the sterile processing department in containers and manually moved e.g. on a trolley to a pre-washing table. At the pre-washing table the medical equipment is manually pre-washed. The pre-washed medical equipment is then arranged in a new container and the new container is manually moved to a washing machine. Next, the washed medical equipment is arranged in a sterilization container and manually moved to an autoclave for sterilization.

The process involves the use of a significant number of different containers having different dimensions.

Thus it remains a problem to provide a system that can aid in automating processes in a sterile processing department capable of handling a plurality of different types of containers.

SUMMARY

According to a first aspect, the invention relates to a transport system for handling a plurality of different types of containers for medical equipment in a sterile processing department for sterilizing medical equipment, the system comprises:
 a plurality of containers of a first type with first outer dimensions and a plurality of containers of a second type with second outer dimensions, the first outer dimensions being different from the second outer dimensions;
 conveyor stations for the plurality of containers, the conveyor stations being configured to transport the first type of containers and/or the second type of containers relative to the conveyor station;
 a transport tray for supporting the first type of containers and the second type of containers, the transport tray having a set of securing elements configured to releasably secure the first type of containers to the transport tray and the second type of containers to the transport tray;
wherein the conveyor station is configured to transport the first type of containers and/or the second type of containers secured to the transport tray.

Consequently, by providing the system with a transport tray a plurality of different types of containers may easily be handled. This further enables the conveyor stations to be more standardized e.g. so that a conveyor station assisting in transporting medical equipment from a washing machine to an autoclave may rely on the same conveyer elements as a conveyor station assisting in transporting used medical equipment to the pre-washing table even thou the type of containers are significantly different.

The first and second type of containers may comprise a bottom, four walls and a lid, where the four walls protrude from the bottom. Examples of containers are transport containers for transporting used medical equipment to the sterile processing department, washing containers for supporting the medical equipment in a washing machine and sterilizing containers for supporting the medical equipment in an autoclave. The conveyor station may be any station capable of transporting containers relative to the conveyor station e.g. using conveyor rolls or a conveyor belt. The conveyor station may be stationary e.g. bolted to the floor. However, the conveyor station may also itself be movable e.g. the conveyor station may be arranged on top of an automatic guided vehicle (AGV). As an example the conveyor station may be an AGV provided with conveyor rolls, where the conveyor rolls are used for loading and/or unloading a container secured to a transport tray and the AGV is used for driving the container from a first part of a sterile processing department to a second part e.g. from pre-washing table to an automated washing machine. The system may comprise a plurality of conveyor stations. The system may comprise one or more control units for controlling the different elements of the system. As an example the system may comprises a control unit operatively coupled to conveyor rolls or a conveyor belt of the conveyor station and configured to control the conveyor rolls or convoy belt. Alternatively, the system may comprise a central control unit operatively connected to a local control unit of the conveyor station, where the local control unit is operatively connected to conveyor rolls or a conveyor belt of the conveyor station and where the central control unit together with the local control unit is configured to control the conveyor rolls or conveyor belt of the conveyor station.

The set of securing elements may comprise one or more protrusions configured to engage with one or more recesses in the bottom of the first type of containers and/or one or more protrusions configured to engage with one or more recesses in the bottom of the second type of containers. Alternatively/additionally, the set of securing elements may comprise one or more recess configured to engage with one or more protrusions of the bottom of the first type of containers and/or one or more recesses configured to engage with one or more protrusions of the second type of containers. The set of securing elements may comprise one or more protrusions configured to engage with an outer surface of a wall of the first type of containers and/or one or more protrusions configured to engage with an outer surface of a wall of the second type of containers.

The set of securing elements may be configured to secure that a container of the first type or the second type is secured to a transport tray cannot move in the horizontal plane relative to the transport tray while allowing the container to be freely lifted from the transport tray. This will make it easier to automatically arrange a container on a transport tray and automatically remove a container from a transport tray e.g. using a robotic arm.

The set of securing elements may comprises a first subset of securing elements configured to releasably secure the first type of containers to the transport tray and a second subset of securing element configured to releasably secure the second type of containers to the transport tray. The first subset is different from the second subset but may have one or more securing elements in common.

In some embodiments the first type of containers or the second type of containers is sterilization containers configured to be autoclaved.

In some embodiments the first type of containers are sterilization containers configured to be autoclaved and the second type of containers is washing containers for supporting the medical equipment in an automated washing machine.

In some embodiments the conveyor station comprises a plurality of conveyor rolls and/or a conveyor belt.

In some embodiments the conveyor station comprises three conveyor rolls, the first type of containers and the transport tray have a width, a length and a height, the length of the transport tray being at least 20% longer than the length of the first type of containers and the length of the transport tray having a length equal to or longer that the distance between the center of any two of the three conveyor rolls whereby the transport tray may be supported by each of the three conveyor rolls at the same time.

Consequently, by using a transport tray that effectively enlarges the support surface of the containers, conveyor rolls may be used without vibrating or shaking the medical equipment in the containers. This will reduce the noise level significantly, since the medical equipment often comprises metal parts and the containers often also are made of metal. Thus, the work environment of the sterile processing department is improved.

In some embodiments, the conveyor rolls are motorized conveyor rolls configured to propel the container secured to the transport tray.

In some embodiments the transport tray has at least two dimensions that are longer than the one or more containers e.g. at least 10%, 20% or 30% longer.

In some embodiments a first conveyor station of the one or more conveyor stations comprises a plurality of conveyor rolls and one or more support elements, the one or more support elements being movable from a resting position to a receiving position, the one or more support elements having a support surface for supporting the first type of containers and/or the second type of containers, the support surface of the one or more support elements being lower than the highest point of the plurality of conveyer rolls when positioned in the resting position and higher than the highest point of the plurality of conveyer rolls when positioned in the receiving position, and wherein the system is configured to:
  arrange a first container of the first type or the second type on the first conveyor station by moving the one or more support element to the receiving position, arranging the first container on the support surface of the one or more support elements and subsequently moving the one or more support elements to the resting position; and/or
  transfer the first container away from the first conveyor station by transporting the first container using the plurality of conveyor rolls above the one or more support elements being in the resting position moving the one or more support elements to the receiving position whereby the first container is lifted from the plurality of conveyor rolls and subsequently moving the first container away from the first conveyor station.

Consequently, a container may be arranged on a conveyor station or transferred away in a simple and effective manner allowing the container to be supported from below when being transported to and from the conveyor station. This may further make it easier to automatically transfer a container on the conveyer station.

The one or support elements may be connected to an actuator e.g. a linear actuator configured to move the one or more support elements from the resting position to the receiving position and vice versa.

The first conveyor station may comprise a plurality of support elements e.g. at least three support elements for supporting a bottom of the first container in a stable manner. At least one of the plurality of support elements may be arranged between two conveyor rolls of the plurality of conveyor rolls. The plurality of support elements may be connected to a single linear actuator via a connection element. The first conveyor station may comprise a first set of support elements configured to receive containers and a second set of support elements configured to transfer containers away from the first conveyor station.

The system may comprise one or more control units configured to control the one or more support elements of the first conveyor station e.g. a control unit may be operatively coupled to an actuator and configured to firstly control the actuator to move the one or more support elements to the receiving position and then secondly after a container has been arranged on the one or more support elements control the actuator to move the one or more support elements to the resting position.

In some embodiments the transport tray has one or more openings, the system being configured align the one or more openings with the one or more support elements, before moving the one or more support elements from the resting position to the receiving position when receiving a container or transferring a container whereby the one or more support elements extend through the one or more openings when moved to the receiving position.

Consequently, a container may in a single simple operation both be arranged on a support tray and on a conveyor station or transferred away from both a transport tray and a conveyor station.

The transport tray may comprise a plurality of opening e.g. at least 2, 3, 4, or 5 openings, where the plurality of opening are arranged on the transport tray in manner whereby the plurality of opening are covered by a bottom surface of both a container of the first type arranged on the tray and a container of the second type arranged on the tray, whereby both types of containers may be transferred to and from the tray using the plurality of support elements. In some embodiments the transport tray has one or more openings, the system being configured arrange the first container on the transport tray and the first conveyor station by arranging the transport tray on the first conveyor station in manner whereby the one or more openings of the transport tray are aligned with the one or more support elements, moving the one or more support elements to the receiving position whereby they extend through the one or more openings and subsequently moving the one or more support elements to the resting position after the first container has been arranged on the support surface of the one or more support elements whereby the first container is both arranged at the first conveyor station and secured to the transport tray.

In some embodiments the system further comprises a robotic arm, the robotic arm being configured to pick-up the first container and arrange the first container on the one or more support elements and/or transfer the first container away from the one or more support elements.

Consequently, the operation of arranging a container on a support tray and on a conveyor station or transferring a container from a support tray and a conveyor station may be fully automated.

The first container may be stored in a rack holding a plurality of containers before being picked up by the robotic arm. The system may comprise a control unit configured to control the robotic arm e.g. the control unit may be operatively connected to the robotic arm and configured to control the robotic arm.

The robotic arm may be configured to secure that the first container is arranged on the one or more support elements in a position so that the first container is engaging with the set of securing elements of the support tray when the one or more support elements moves to the resting position, whereby the first container is secured to the support tray.

In some embodiments the robotic arm comprises one or more lifting elements and wherein the robotic arm is configured to pick-up the first container by sliding the one lifting elements under the first container whereby the bottom of the first container rests on the one or more lifting elements of the robotic arm.

In some embodiments the robotic arm is further configured to pick-up the transport tray and arrange the transport tray on the plurality of conveyor rolls of the first conveyor station.

In some embodiments the robotic arm is further configured to align the one or more openings of the transport tray with the one or more support elements.

In some embodiments a plurality of transport trays are arranged in a stack, and wherein the robotic arm is configured to pick-up the transport tray from the stack.

According to a second aspect the invention relates to a transport tray for use in a transport system as disclosed in relation to the first aspect, the transport system comprising a plurality of containers of a first type with first outer dimensions and a plurality of containers of a second type with second outer dimensions, the first outer dimensions being different from the second outer dimensions, wherein the transport tray has a set of securing elements configured to releasably secure the first type of containers to the transport tray and the second type of containers to the transport tray.

The set of securing elements may comprise one or more protrusions configured to engage with one or more recesses in the bottom of the first type of containers and/or one or more protrusions configured to engage with one or more recesses in the bottom of the second type of containers. Alternatively/additionally, the set of securing elements may comprise one or more recess configured to engage with one or more protrusions of the bottom of the first type of containers and/or one or more recesses configured to engage with one or more protrusions of the second type of containers. The set of securing elements may comprise one or more protrusions configured to engage with an outer surface of a wall of the first type of containers and/or one or more protrusions configured to engage with an outer surface of a wall of the second type of containers.

The set of securing elements may be configured to secure that a container of the first type or the second type secured to a transport tray cannot move in the horizontal plane relative to the transport tray while allowing the container to be freely lifted from the transport tray. This will make it easier to automatically arrange a container on a transport tray and automatically remove a container from a transport tray e.g. using a robotic arm.

The set of securing elements may comprises a first subset of securing elements configured to releasably secure the first type of containers to the transport tray and a second subset of securing element configured to releasably secure the first type of containers to the transport tray. The first subset is different from the second subset but may have one or more securing elements in common.

In some embodiments the transport tray further comprises one or more openings for receiving one or more movable support elements of a conveyer station.

In some embodiments the transport tray comprises further one or more handles for transporting the transport tray.

According to a third aspect the invention relates to a sterile processing department comprising a transport system as disclosed in relation to the first aspect of the invention.

The different aspects of the present invention can be implemented in different ways including as a transport system, a transport tray, and a sterile processing department described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependent claims.

Furthermore, it will be appreciated that embodiments described in connection with one of the aspects described herein may equally be applied to the other aspects.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
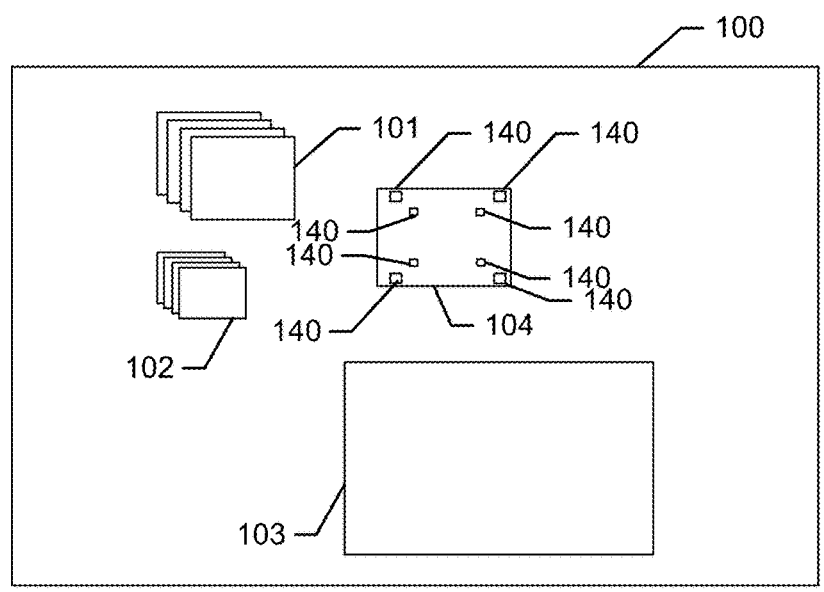
FIG. 1 shows a schematic drawing of a transport system for handling a plurality of different types of containers for medical equipment in a sterile processing department according to an embodiment of the present invention.

FIG. 1 shows a schematic drawing of a transport system 100 for handling a plurality of different types of containers for medical equipment in a sterile processing department for sterilizing medical equipment according to an embodiment of the present invention. The transport system comprises a plurality of containers of a first type 101 with first outer dimensions and a plurality of containers of a second type with second outer dimensions 102, the first outer dimensions being different from the second outer dimensions. The transport system 100 further comprise conveyor stations 103 for the plurality of containers 101 102, the conveyor stations 103 being configured to transport the first type of containers 101 and/or the second type of containers 102 relative to the conveyor station 103; and a transport tray 104 for supporting the first type of containers 101 and the second type of containers 102. The transport tray 104 has a set of securing elements 140 configured to releasably secure the first type of containers 101 to the transport tray and the second type of containers 102 to the transport tray. The conveyor station 103 is configured to transport the first type of containers 101 and/or the second type of containers 102 secured to the transport tray 104.

Only a single conveyor station 103 is shown, however the transport system may comprise a plurality of conveyor stations e.g. a first conveyor station configured to transport used medical equipment towards a pre-washing table where the used medical equipment is manually pre-washed by a person, a second conveyor station for transporting the pre-washed medical equipment from the pre-washing table towards an automated washing machine, and a third conveyor station for transporting the washed medical equipment towards an autoclave. As an example the first type of containers 101 may be containers configured to transport used medical equipment from e.g. an operating room to a pre-washing table e.g. using the first conveyor station (at least for transporting the used medical equipment the last 0.2 meter preferably at least the last 0.5 meter), and the second type of containers 102 may be configured to both support the medical equipment in an automated washing machine and an autoclave e.g. the medical equipment may be supported in a container of the second type 102 without a lid in the automated washing machine and a container of the second type with a special autoclave lid designed to allow hot steam to enter the container when in the autoclave. Thus, the medical equipment may be carried in the second type of container 102 when it is transported using the second conveyor station and the third conveyor station.

However, the transport system may also comprise a third type of container, where the second type is only configured to support the medical equipment in the automated washing machine and where the thirds type of container is a sterilizing container configured to support the washed medical equipment in the autoclave. The sterile processing department may further comprise a packing station where the washed medical equipment is packed into the third type of containers, thus the third conveyor station will then transport the medical equipment from the automated washing machine towards the packing station (but as the packing station is on the route to the autoclave the third conveyor station will still transport the medical equipment towards the autoclave). The transport system will then further comprise a fourth conveyor station configured to transport the medical equipment from the packing station towards the autoclave. The first, second, third and/or fourth conveyor stations may be stationary e.g. bolted to the floor or they may be movable e.g. they may be arranged on top of an AGV. The transport system may comprise a combination of stationary and movable conveyor stations e.g. the first, and second conveyor station may be stationary and where the transport system further comprises a fifth and a sixth movable conveyor stations configured to load and un-load containers at the first and second conveyor stations. Using a transport tray configured to releasably secure the first type 101, second type 102 and third type of containers to the transport tray, the different conveyor station may be standardized e.g. use the same conveyor rolls making them simpler to produce and maintain. The use of the transport tray will furthermore increase the flexibility of the transport system as the transport tray relatively simple may be adapted to a new type of container.

Figures 2A, 3A, 4A:
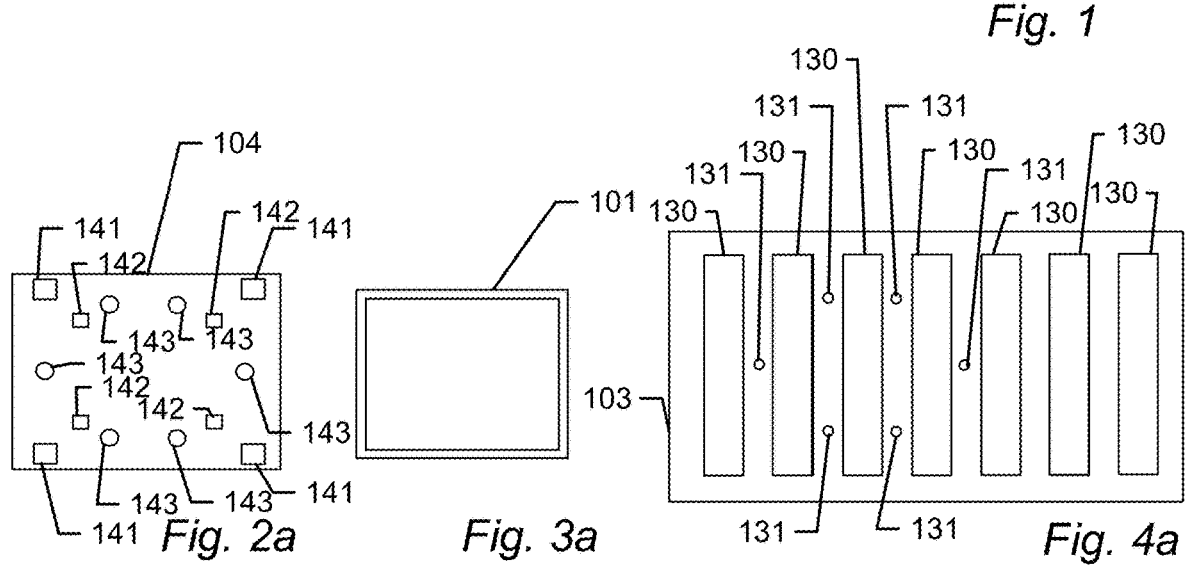
FIGS. 2*a-b* show a schematic drawing of a transport tray according to an embodiment of the present invention.
FIGS. 3*a-b* show a schematic drawing of a container for medical equipment according to an embodiment of the present invention.
FIGS. 4*a-b* show a schematic drawing of a conveyor station according to an embodiment of the present invention.
Figures 2B, 3B, 4B:
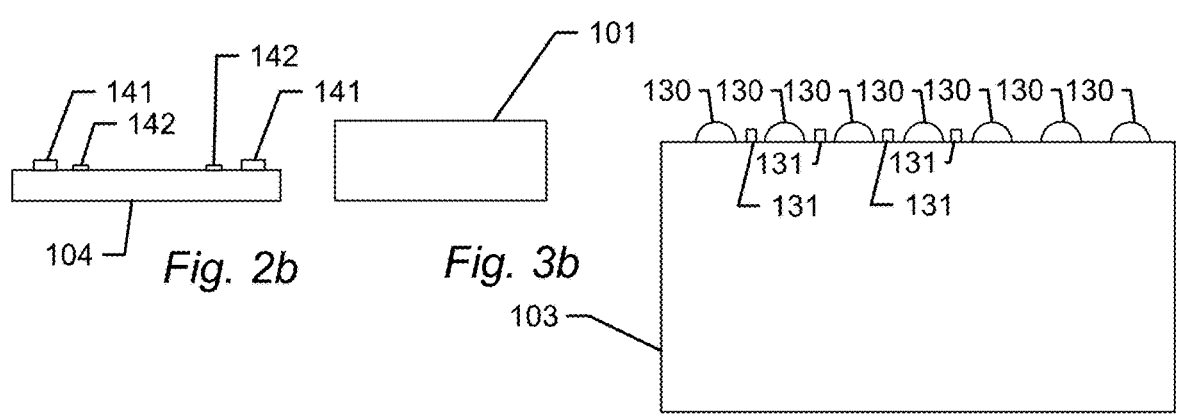

FIGS. 2a-b show a schematic drawing of a transport tray 104 according to an embodiment of the present invention, where FIG. 2a shows a top view and FIG. 2b shows a side view. The transport tray 104 comprises a set of securing elements 141 142 configured to releasably secure a first type of container to the transport tray and a second type of container to the transport tray 104. The set of securing elements 141 142 comprises a first subset of securing elements 141 configured to releasably secure the first type of containers to the transport tray and a second subset of securing element 142 configured to releasably secure the first type of containers to the transport tray. The transport tray 104 comprises further six opening 143 for receiving support elements of a conveyor station.

FIGS. 3a-b show a schematic drawing of a container 101 for medical equipment according to an embodiment of the present invention, where FIG. 3a shows a top view and FIG. 3b shows a side view. The container 101 comprises a bottom and four walls protruding from the bottom. The container 101 is shown without a lid and empty. The container 101 will typically contain medical equipment.

FIGS. 4a-b show a schematic drawing of a conveyor station 103 according to an embodiment of the present invention, where FIG. 4a shows a top view and FIG. 4b shows a side view. The conveyor station 103 comprises in this embodiment seven motorized conveyor rolls 130 and six support elements 131.

Figure 5A:
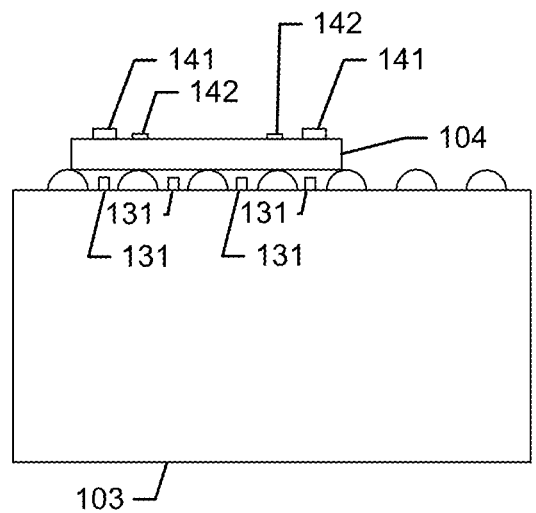
FIGS. 5*a-d* are schematic drawings illustrating how a container may be secured to a transport tray arranged on a conveyor station according to an embodiment of the present invention.
Figure 5B:
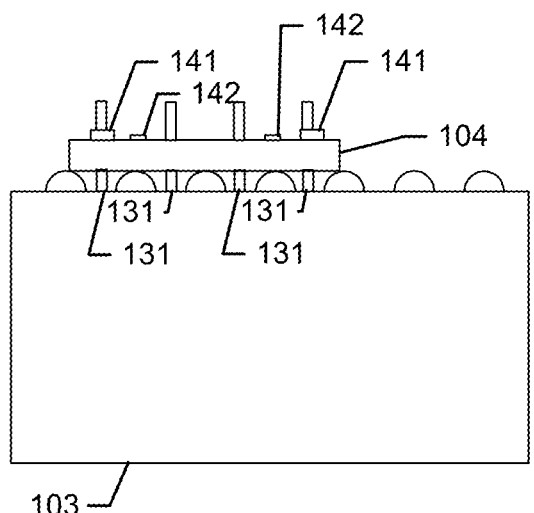
Figure 5C:
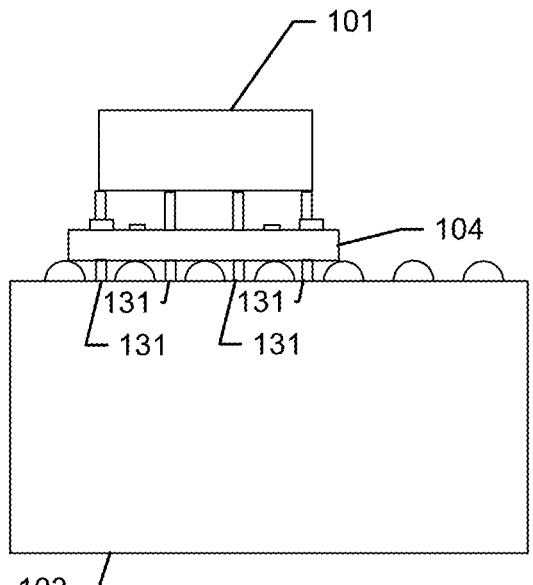
Figure 5D:
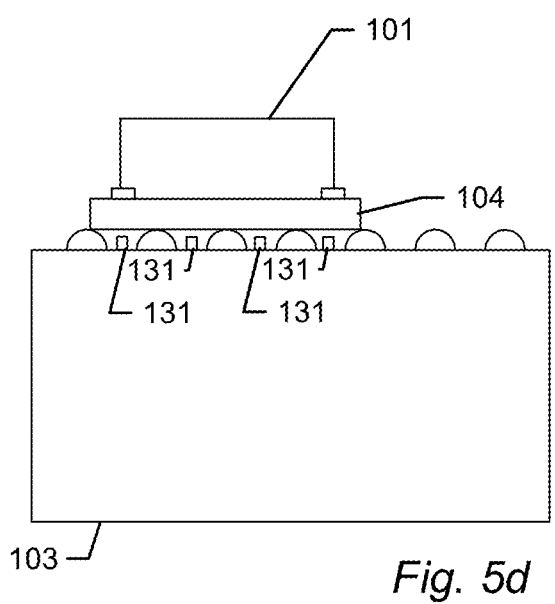

FIGS. 5a-d are schematic drawings of a transport system illustrating how a container 101 may be secured to a transport tray 104 arranged on a conveyor station 103 according to an embodiment of the present invention. The container 101 corresponds to the container shown in FIG. 3a-b, the transport tray 104 corresponds to the transport tray 104 shown in FIG. 2a-b, and the conveyor station 103 corresponds to the conveyor station 103 shown in FIG. 4a-b. FIG. 5a-d shows the system in a side view at different points in time. FIG. 5a shows the transport system at a first point in time, with the transport tray 104 arranged on the conveyor station 103, and with the six openings 142 of the transport tray 104 aligned with the six support elements 131 of the conveyor station 103. At the first point in time, the six support elements 131 are arranged in a resting position. FIG. 5b shows the system at a second point in time, after the first point in time, where the six support elements 131 are moved from their resting position to their receiving position, whereby they extend through the six openings 142 of the transport tray 104. FIG. 5c shows the system at a third point in time, after the second point in time, where the container 101 is arranged on support surfaces of the six support elements 131. FIG. 5d shows the system at a fourth point in time, after the third point in time, where the six support elements 131 are moved back to their resting position whereby first container 101 is both arranged at the conveyor station 103 and secured to the transport tray 104.

Figure 6:
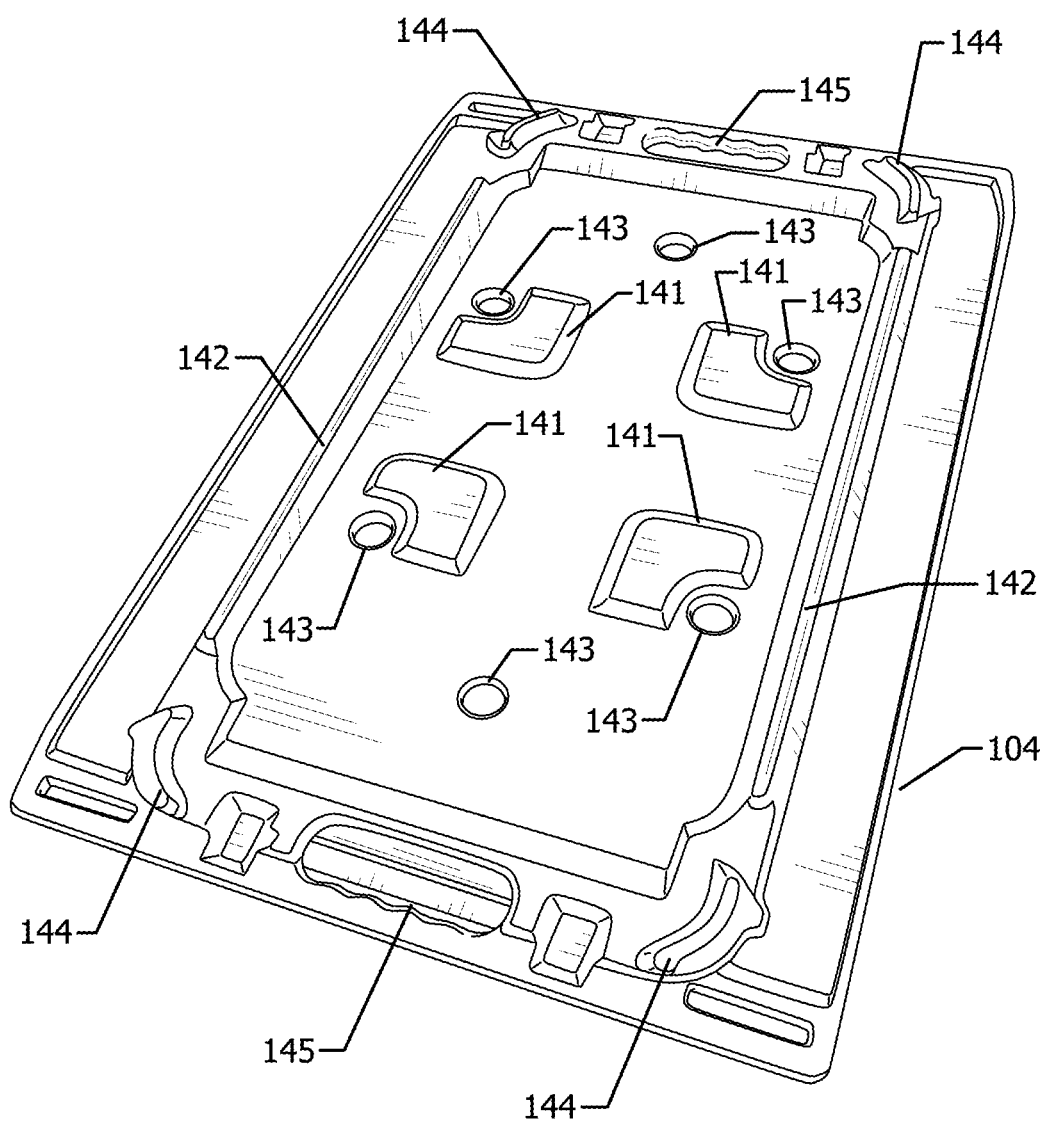
FIG. 6 shows a perspective view of a transport tray 104 for use in a transport system according to an embodiment of the invention.

FIG. 6 shows a perspective view of a transport tray 104 for use in a transport system according to an embodiment of the invention. The system comprises a plurality of containers of a first type with first outer dimensions and a plurality of containers of a second type with second outer dimensions, the first outer dimensions being different from the second outer dimensions. The transport tray has a set of securing elements 141 142 144 configured to releasably secure the first type of containers to the transport tray 104 and the second type of containers to the transport tray 104. The set of securing element 141 142 144 comprises a first subset of securing elements 144 configured to releasably secure the first type of containers to the transport tray and a second subset of securing elements 141 configured to releasably secure the second type of containers to the transport tray 104. In this embodiment the first subset of securing elements 144 comprises four protrusions configured to engage with an outer surface of a wall of the first type of containers and the second subset of securing elements 141 comprises four protrusions configured to engage with four recesses in the bottom of the second type of containers. In this embodiment the set of securing elements 141 142 144 further comprises a third subset 142 of securing elements comprising two elongated protrusions 142 configured to engage with an outer surface of a wall of a third type of containers. The support tray 104 comprises further six openings 143 configured to received six support elements of a conveyor station as explained in relation to FIGS. 5a-d.

Figure 7:
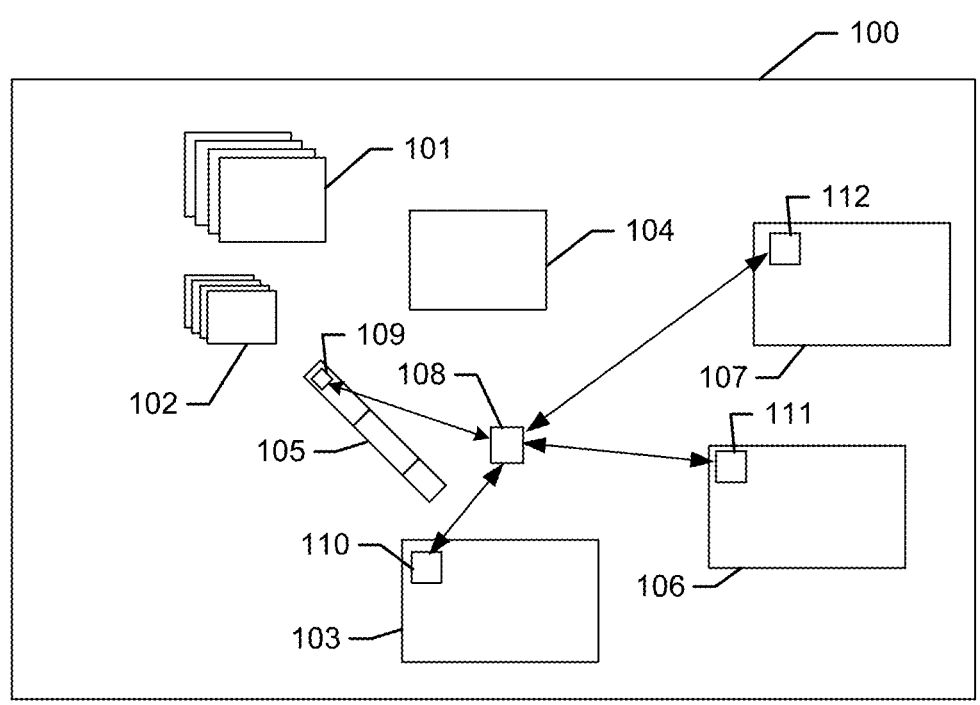
FIG. 7 shows a schematic drawing of a transport system for handling a plurality of different types of containers for medical equipment in a sterile processing department according to an embodiment of the present invention.

FIG. 7 shows a schematic drawing of a transport system 100 for handling a plurality of different types of containers for medical equipment in a sterile processing department for sterilizing medical equipment according to an embodiment of the present invention. The transport system 100 comprises a plurality of containers of a first type 101 with first outer dimensions and a plurality of containers of a second type with second outer dimensions 102, the first outer dimensions being different from the second outer dimensions. The transport system 100 further comprise a first conveyor stations 103, a second conveyor station 106 and a third conveyor station 107. The first, second and third conveyor station 103 106 107 are configured to transport the first type of containers 101 and/or the second type of containers 102 relative to them self. The system 100 further comprises a transport tray 104 for supporting the first type of containers 101 and the second type of containers 102. The first, second and third conveyor station 103 106 107 are configured to transport the first type of containers 101 and/or the second type of containers 102 secured to the transport tray 104. One or more of the three conveyor stations 103 106 107 may be a stationary conveyor station and one or more of the three conveyor stations 103 106 107 may be a movable conveyor station e.g. an AGV having conveyor rolls arranged on top. The system 100 further comprises a robotic arm 105 configured to arranged a container of the first type 101 and/or a container of the second type 102 on one or more of the three conveyor stations 103 106 107. The robotic arm 105 may further be configured to arranged the transport tray 104 on one or more of the three conveyor stations 103 106 107. The system comprises further a central control unit 108 operatively connected to control units 110 111 112 of the three conveyor stations 103 106 107 and a control unit 109 of the robotic arm 105. As an example the central control unit 108 may send signal to the control unit 109 of the robotic arm 105 controlling the robotic arm 105 to arrange the transport tray 104 on the conveyor station 103. Next, the central control unit may send a control signal to the control unit 110 of the conveyor station 103 controlling the conveyor station to raise support elements to their receiving position as shown in FIG. 5b. Next, the central control unit 108 may send a control signal to the robotic arm 105 controlling the robotic arm 105 to pick up a container of the first type 101 and arranged the container on the support surfaces of the support elements as shown in FIG. 5c. Then, the central control unit 108 may send a control signal to the control unit 110 of the conveyor station 103 controlling the conveyor station 103 to move the support elements back to their resting position as shown in FIG. 5d and subsequently activate motorized convoy rolls of the conveyor station whereby the container of the first type 101 secured to the transport tray 104 is transported relative to the conveyor station 103.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A transport system for handling a plurality of different types of containers for medical equipment in a sterile processing department for sterilizing medical equipment, the system comprises:
  a plurality of containers of a first type with first outer dimensions and a plurality of containers of a second type with second outer dimensions, the first outer dimensions being different from the second outer dimensions;
  a conveyor station for the plurality of containers, the conveyor station being configured to transport the first type of containers and/or the second type of containers relative to the conveyor station;
  a transport tray for supporting the first type of containers and the second type of containers, the transport tray having a set of securing elements configured to releasably secure the first type of containers to the transport tray and the second type of containers to the transport tray;
  wherein the conveyor station is configured to transport the first type of containers and/or the second type of containers secured to the transport tray; and
  wherein the first type of containers are sterilization containers configured to be autoclaved and the second type of containers is washing containers for supporting the medical equipment in an automated washing machine.

2. The system according to claim 1, wherein the set of securing elements comprises a first subset of securing elements configured to releasably secure the first type of containers to the transport tray and a second subset of securing element configured to releasably secure the second type of containers to the transport tray.

3. A transport system for handling a plurality of different types of containers for medical equipment in a sterile processing department for sterilizing medical equipment, the system comprises:
- a plurality of containers of a first type with first outer dimensions and a plurality of containers of a second type with second outer dimensions, the first outer dimensions being different from the second outer dimensions;
- a conveyor station for the plurality of containers, the conveyor station being configured to transport the first type of containers and/or the second type of containers relative to the conveyor station;
- a transport tray for supporting the first type of containers and the second type of containers, the transport tray having a set of securing elements configured to releasably secure the first type of containers to the transport tray and the second type of containers to the transport tray;
- wherein the conveyor station is configured to transport the first type of containers and/or the second type of containers secured to the transport tray;
- wherein the conveyor station comprises three conveyor rolls, the first type of containers and the transport tray have a width, a length and a height, the length of the transport tray being at least 20% longer than the length of the first type of containers and the length of the transport tray having a length equal to or longer that the distance between the center of any two of the three conveyor rolls whereby the transport tray may be supported by each of the three conveyor rolls at the same time.

4. A transport system for handling a plurality of different types of containers for medical equipment in a sterile processing department for sterilizing medical equipment, the system comprises:
- a plurality of containers of a first type with first outer dimensions and a plurality of containers of a second type with second outer dimensions, the first outer dimensions being different from the second outer dimensions;
- a conveyor station for the plurality of containers, the conveyor station being configured to transport the first type of containers and/or the second type of containers relative to the conveyor station;
- a transport tray for supporting the first type of containers and the second type of containers, the transport tray having a set of securing elements configured to releasably secure the first type of containers to the transport tray and the second type of containers to the transport tray;
- wherein the conveyor station is configured to transport the first type of containers and/or the second type of containers secured to the transport tray;
- wherein a first conveyor station of the one or more conveyor stations comprises a plurality of conveyor rolls and one or more support elements, the one or more support elements being movable from a resting position to a receiving position, the one or more support elements having a support surface for supporting the first type of containers and/or the second type of containers, the support surface of the one or more support elements being lower than the highest point of the plurality of conveyer rolls when positioned in the resting position and higher the highest point of the plurality of conveyer rolls when positioned in the receiving position, and wherein the system is configured to:
- arrange a first container of the first type or the second type on the first conveyor station by moving the one or more support element to the receiving position, arranging the first container on the support surface of the one or more support elements and subsequently moving the one or more support elements to the resting position; and/or
- transfer the first container away from the first conveyor station by transporting the first container using the plurality of conveyor rolls above the one or more support elements being in the resting position moving the one or more support elements to the receiving position whereby the first container is lifted from the plurality of conveyor rolls and subsequently moving the first container away from the first conveyor station.

5. The system according to claim 4, wherein the transport tray has one or more openings, the system being configured align the one or more openings with the one or more support elements, before moving the one or more support elements from the resting position to the receiving position when receiving a container or transferring a container whereby the one or more support elements extend through the one or more openings when moved to the receiving position.

6. The system according to claim 4, wherein the system further comprises a robotic arm, the robotic arm being configured to pick-up the first container and arrange the first container on the one or more support elements and/or transfer the first container away from the one or more support elements.

7. The system according to claim 6, wherein the robotic arm comprises one or more lifting elements and wherein the robotic arm is configured to pick-up the first container by sliding the one lifting elements under the first container whereby the bottom of the first container rests on the one or more lifting elements of the robotic arm.

8. The system according to claim 7, wherein the robotic arm is further configured to pick-up the transport tray and arrange the transport tray on the plurality of conveyor rolls of the first conveyor station.

9. The system according to claim 8, wherein the robotic arm is further configured to align the one or more openings of the transport tray with the one or more support elements.

10. The system according to claim 8, wherein a plurality of transport trays are arranged in a stack, and wherein the robotic arm is configured to pick-up the transport tray from the stack.

11. A transport tray, comprising;
- a set of securing elements configured to releasably secure a first type of containers to the transport tray and a second type of containers to the transport tray, the first type of containers having first outer dimensions different from second outer dimensions of the second type of containers; and
- one or more openings for receiving one or more movable support elements of a conveyer station.

12. The transport tray according to claim 11, wherein the set of securing elements comprises a first subset of securing elements configured to releasably secure the first type of containers to the transport tray and a second subset of securing element configured to releasably secure the second type of containers to the transport tray.

* * * * *